United States Patent

Hsu

[11] Patent Number: 6,072,705
[45] Date of Patent: Jun. 6, 2000

[54] POWER SOURCE CONVERSION DEVICE CAPABLE OF ELIMINATING LOW-FREQUENCY RADIATION

[75] Inventor: Yuan-Fang Hsu, Hsinchu, Taiwan

[73] Assignee: Chin-Tong Liu, Hsin-Chu, Taiwan

[21] Appl. No.: 09/348,542

[22] Filed: Jul. 7, 1999

[51] Int. Cl.[7] .................................................. H02J 1/02
[52] U.S. Cl. ............................ 363/39; 361/110; 439/106
[58] Field of Search ............................ 363/39, 44, 50, 363/52; 439/106, 101, 105, 650; 361/42–50, 110, 111, 119

[56] References Cited

U.S. PATENT DOCUMENTS

| | | | |
|---|---|---|---|
| 3,958,849 | 5/1976 | Blairsdale | 439/104 |
| 4,078,848 | 3/1978 | Blairsdale | 439/103 |
| 4,506,260 | 3/1985 | Woodruff et al. | 340/649 |
| 5,658,158 | 8/1997 | Milan | 439/214 |
| 5,684,689 | 11/1997 | Hahn | 363/146 |
| 5,788,521 | 8/1998 | Milan | 439/214 |

*Primary Examiner*—Adolf Denske Berhane
*Assistant Examiner*—Bao Q. Vu
*Attorney, Agent, or Firm*—Smith, Gambrell & Russell, LLP

[57] ABSTRACT power source conversion device capable of eliminating low-frequency radiation consisting of electronic circuit is designed to convent the marketable 2-hole type socket power source into 3-hole type socket so as to restore the characteristics of original 3-hole type power source through human body or electronic appliance housing or referable zero potential point, wherein the third hole is substitutive ground point to develop the effect of electromagnetic screening device built in the electric appliances in general for achieving good grounding and eliminating electromagnetic radiation and effect of electric leakage on human body because of poor insulation or induction, and meantime, through the functions of automatically detecting LIFE and NULL and such lines as actuating, locking, safe and warning, an intelligent power source conversion device with overall functions is well combined.

5 Claims, 5 Drawing Sheets

6,072,705

POWER SOURCE CONVERSION DEVICE CAPABLE OF ELIMINATING LOW-FREQUENCY RADIATION

FIELD OF THE INVENTION

The present invention is related to a power source conversion device capable of eliminating low-frequency radiation, and particularly to a device capable of converting the marketable 2-hole type socket power source into 3-hole type socket power source as a convenient, rapid, safe and effective intelligence type conversion device so as to restore the characteristics of original 3-hole type power source, achieve a fine grounding and further develop the effect of electromagnetic screening device as well as prevent leakage from happening.

BACKGROUND OF THE INVENTION

In the daily ever-competing society, those who can control information are winner of tomorrow; therefore the computer has become a prerequisite, useful and effective tool in the information age: it is more and more widespread that the people use computer to process numerous and complicated data, and nowadays the internet is prevailing, computer plays a very important role which is inseparable form the information procurement and liaison as well as multiplex information, transmission between each other. In the circumstances for along time, the so-called computer syndrome appears, and the working personnel in front of the computer terminals are under the effect and threat of radiation intangibly and unknowingly in general and the pregnant women among them in particular. Now there are the so-called computer goggles and protective nets, but their effect is poor, and in fact, hey can partially screen the electromagnetic waves from the display tube but cannot fully eliminate the threat from radiation effect.

Next, all the electrical appliances including computer will generate the AC electromagnetic waves of 60 Hz very low frequency which is normally called as electromagnetic radiation or low-frequency radiation as soon they as turned on. As a close-distance and long-time operational electrical appliance, the computer generates a low-frequency radiation ranging form 60 Hz to 200 megahertz and having an effect on the human body which is quite concerned about by the medical, scientific and technological professionals. So how to effectively eliminate the electromagnetic radiation of computer becomes a large subject matter to be settled by the computer manufacturers.

With regard to the elimination of computer electromagnetic radiation at the present of time, there are the following two methods:

1. In the aspect of manufacturing factory, it is separated with an electromagnetic screening device which is built in the computer to prevent the electromagnetic radiation generated during the circuit operation; however the expected effect cannot be achieved without a fine grounding measure.
2. In the aspect of user, it is eliminated with a correct housing ground, namely, the electromagnetic radiation is absorbed by the electromagnetic screening device and then eliminated through the housing ground. Even the computer manufacturers designed it very well but the users cannot put it into practice in reality (for example, they use the conventional 2-hole type power source socket),and the original design cannot develop its effect.

Therefore, regardless of the present computer with a built-in electromagnetic screening device or not, and in spite of the grounding device of computer itself able to develop its effect or not, the electromagnetic radiation leakage and existence of computer are directly affected.

Those who frequently contact the computer know that the power source wire plug of computer has three legs wherein two flat legs are NULL and LIFE of power source, and the third leg is round as the ground point of computer housing to let the user develop the effect of electromagnetic screening, to prevent leakage and to lessen the electronic-magnetic radiation not necessarily accepted by the human body to a minimum extent. In Europe, America and a number of advanced countries, the power source has been required to adopt 3-hole type socket wherein one hole is used to connect the ground wire buried in the building itself, it is foolproof that the electrical appliance grounding is quite important. It is regrettable that now many countries including Taiwan region remain using 2-hole type power source socket, so the computer users in general, when installing a computer after purchasing it, have to, first of all, remove the round leg, namely the third leg, from its power source wire plug, then they can smoothly insert it into the 2-hole type socket; however, when the said third leg is removed therefrom, the screening effect of computer electromagnetic radiation is ineffective, and the users continuously suffer the prohibitive electromagnetic radiation since they don't know it.

SUMMARY OF THE INVENTION

The primary object of the present invention is to offer a power source conversion device capable of eliminating low-frequency radiation which consists of electronic circuits to convert the present marketable 2-hole type socket power source into 3-hole type socket power source and restore the characteristics of original 3-hole type power source, wherein the third hole is designed a substitutive ground point so that the electromagnetic screening device built in the electronic appliance can develop its effect and achieve a fine grounding and further eliminate the effect of low-frequency radiation on the human body and prevent the leakage from happening.

The secondary object of the present invention is to disclose a power source conversion device capable of intelligent identification, automatic locking and eliminating low-frequency radiation, which is making use of both detecting and locking circuits to identify LIFE or NULL through the human body electronic appliance housing or referable zero potential point. As soon as it is confirmed it is locked until the power source is cut off and the locking is cleared so that the substitutive ground point of the third hole can be correctly grounded to achieve the purpose of eliminating the effect of low-frequency radiation on the human body.

Another object of the present invention is to offer a power source conversion device capable of safe protection, compulsory grounding and eliminating low-frequency radiation, which is making use of safe circuit, warning circuit, actuating circuit, etc, and in case of circuits generating erroneous operations, the safe circuit protects them, and when the power source is turned on, a buzzing reminds the user to touch actuating or to adopt automatic actuating circuit so as to achieve the purpose of grounding.

DETAILED DESCRIPTION OF THE INVENTION

Figure 1:
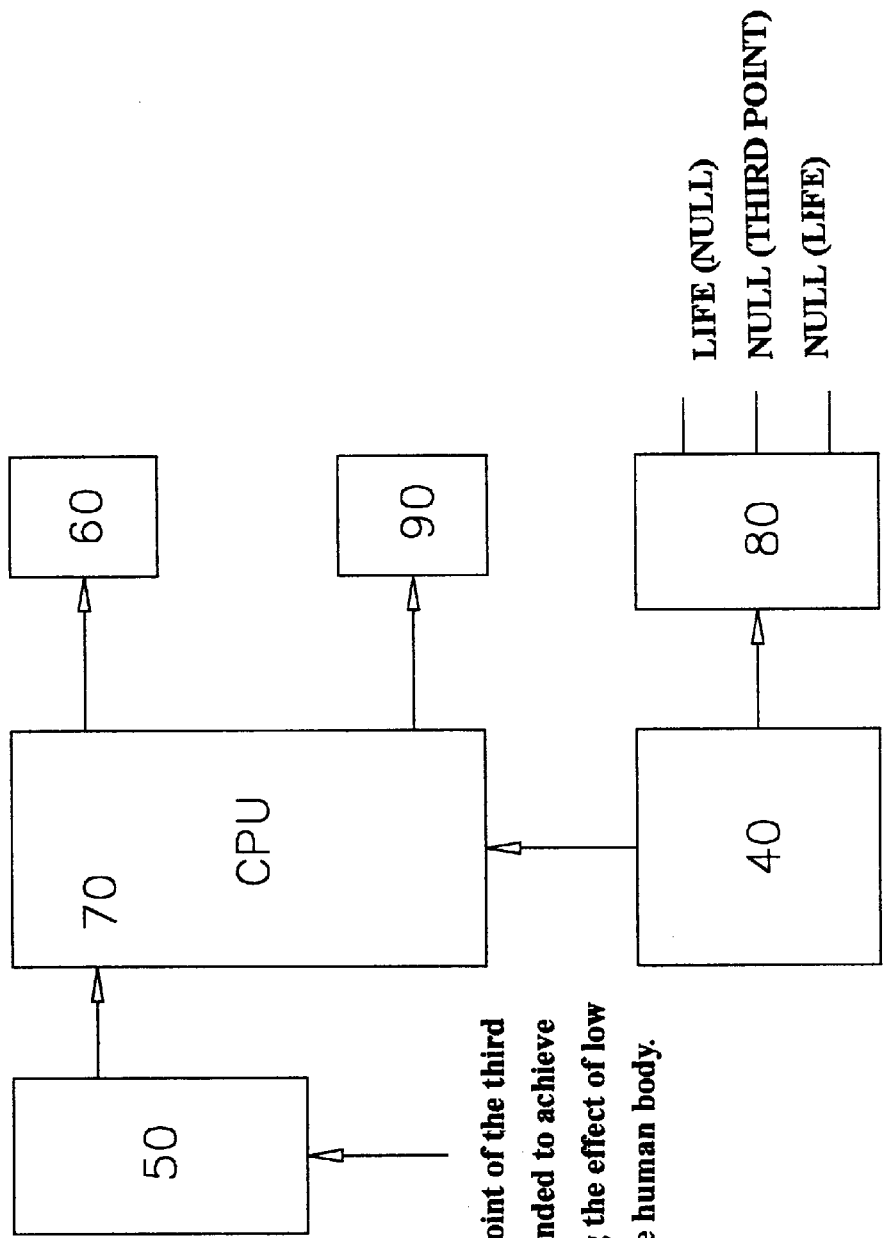
FIG. 1 is a configuration view of the present invention.

As shown in FIG. 1, the present invention is making use of the principle of potential or electromagnetic wave transmission to convert the marketable 2-hole type power source into 3-hole type power source to let the housing for the electric appliance, computer or peripheral equipment so as to develop the effect of screening electromagnetic radiation and let the computer users lessen accepting the unnecessary electromagnetic radiation up to a minimum extent. The present invention adopts the human body or electronic appliance housing or referable zero potential as the reference potential and uses a detecting circuit 50 consisting of electronic circuit to judge which power source wire is LIFE and which wire is NULL. After an actuating circuit 60 is actuated and the said detecting circuit 50 is identified, the NULL is locked by a locking circuit 70 to communicate with the housing ground point (namely the third hole ground point) of electronic appliance or computer power source wire. When the power source of said conversion device is interrupted (for instance, the plug is removed or blockout, the ground point locking is unlocked; and when to use the said appliance or computer, it has to be actuated again or resort to automatic actuating so as to achieve an accurate identification and to avoid an erroneous identification from leading to a danger of personnel suffering electrical shock or computer burning; meantime, the present invention has a safe and protective effect, in case of an erroneous circuit operation, a safe circuit 80 acts as a protector. so the present invention is a convenient, rapid, safe and effective intelligent conversion device.

Figure 2:
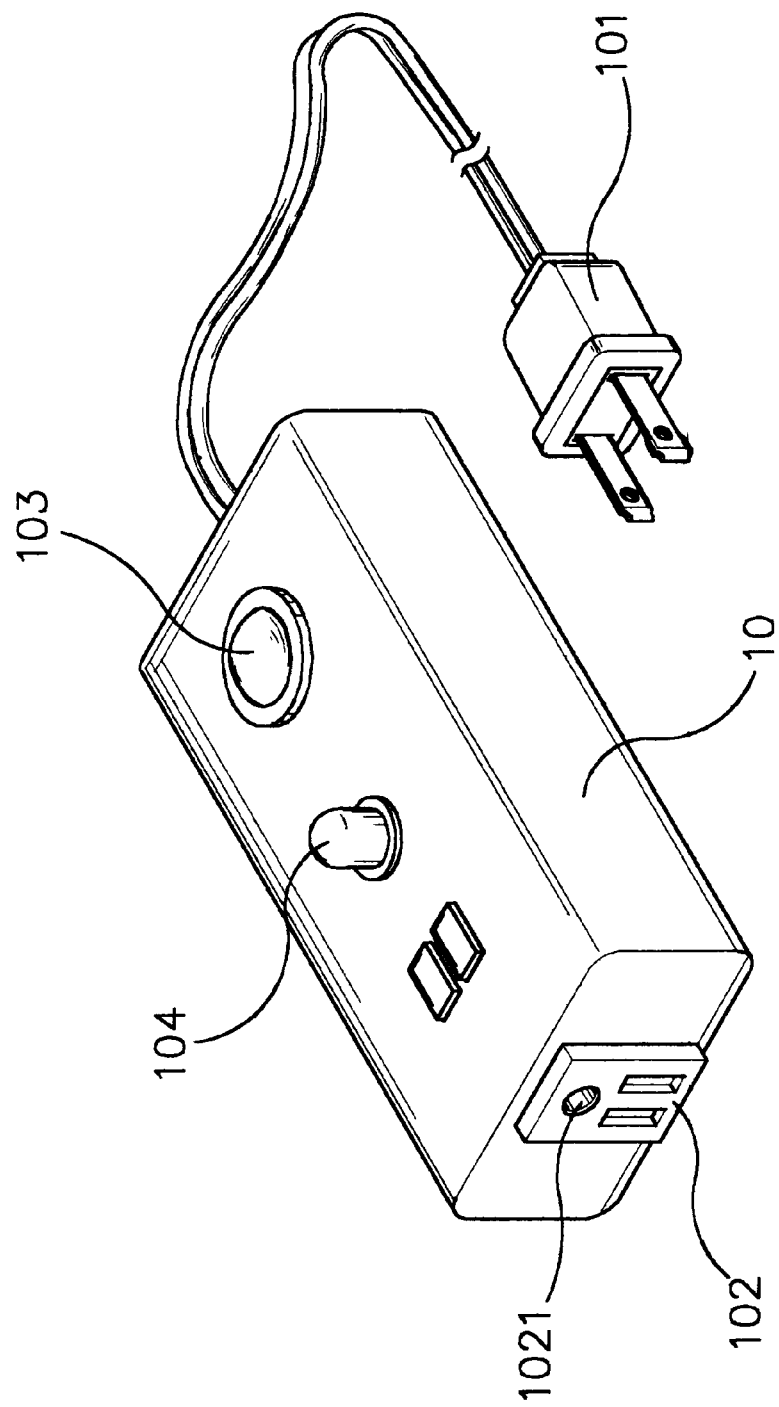
FIG. 2 is the first example of the present invention.
Figure 3:
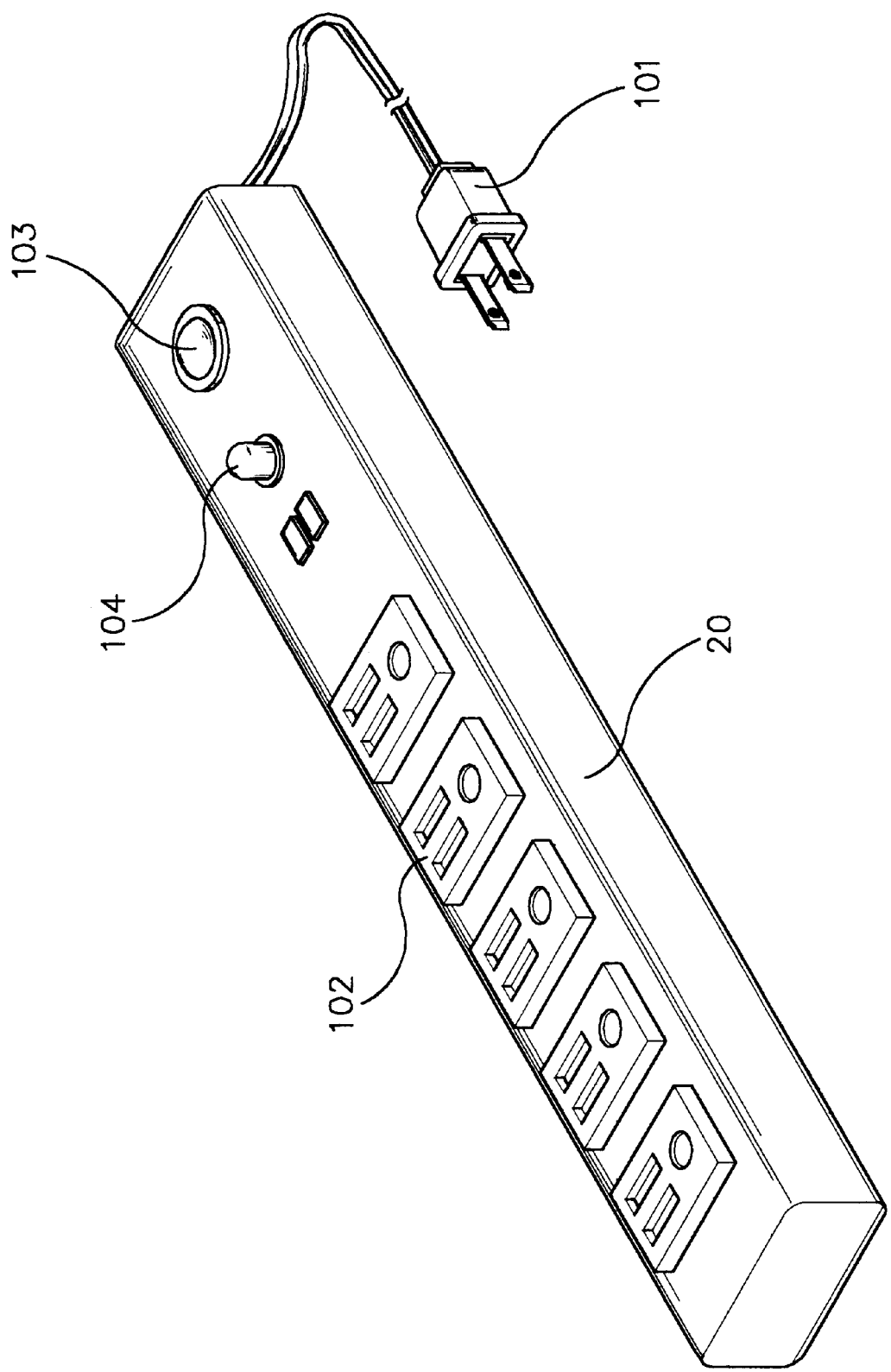
FIG. 3 is the second example of the present invention.
Figure 4:
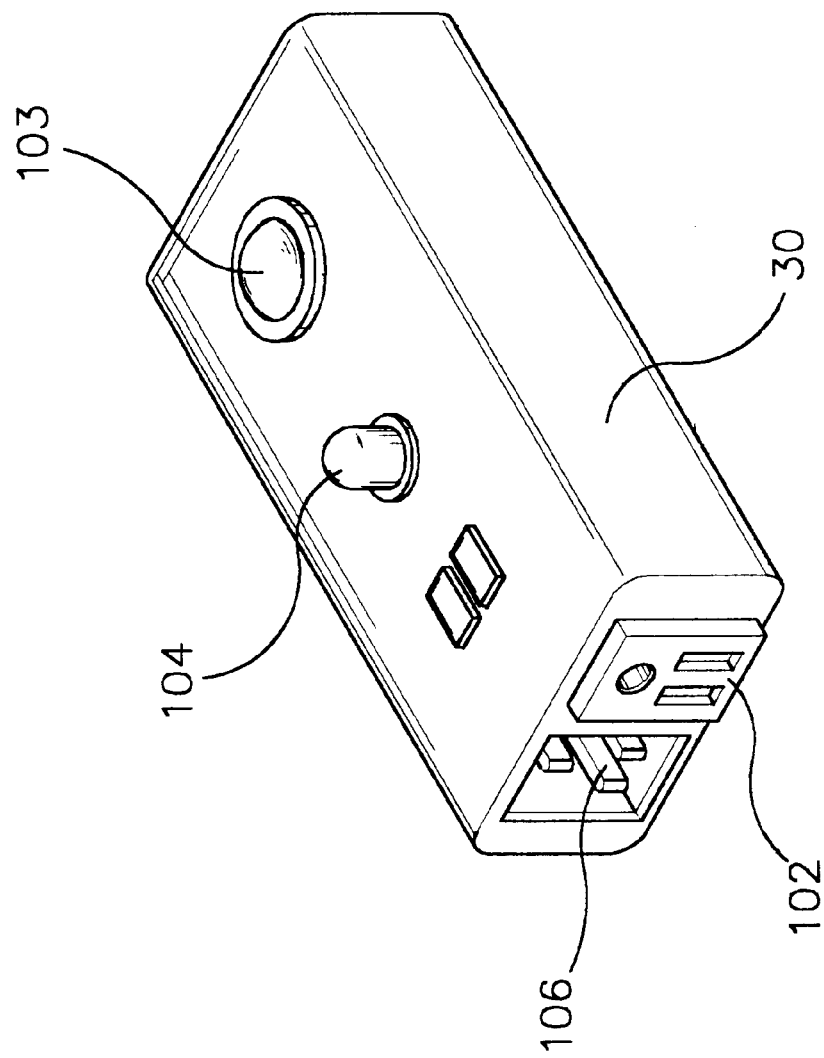
FIG. 4 is the third example of the present invention.

As shown in FIG. 2 to 4. the three examples consist of electronic circuits as shown in FIG. 1; and FIG. 2 shows a power source conversion device I 10 consists of a box body as a pattern of converting a 2-hole type power source plug 101 into a 3-hole type power source socket 102, and a touch point 103 and a power source indicating lamp 104 are on the top side thereof. After the user inserts the power source plug 101 into a 2-hole type socket on the wall, the present invention has not been actuated, so a warning circuit 90 in the said box body is buzzing, and the indicating lamp 104 twinkles to remind the user to touch the touch point 103 or await automatic or actuating. If the user touches the touch point 103 resorts to the housing or referable potential point for automatic actuating, the detecting circuit 50 starts to identify, and at this time, if the life position is found out and another wire is detected and confirmed as the NULL of power source, a round ground point 1021 of power source socket 102 is locked by the locking circuit 70 onto the NULL, and the indicating lamp stops twinkling. If the computer power source plug is inserted into the 3-hole type power source socked 102, the housing ground point (the third point) of said power source plug communicates with the originally locked NULL so as to achieve the purpose of computer housing entirely grounding and the effect of electromagnetic radiation leakage and electric leakage avoidable.

FIG. 3 shows a pattern of the present invention connected to a foreign power source extension wire, namely power source conversion device II 20 capable of grounding the housing as mentioned above, the difference consists in a plurality of 3-hole type power source sockets 102 arranged in parallel so as to achieve the requirement for a multiple power source grounding. FIG. 4 shows another example of the present invention without power source wire and plug but with an assembly of a convex 3-hole type power source socked 102 and a concave socked 106 as a power source conversion device III 30 which can achieve the purpose of housing grounding as that set forth in FIG. 2 but has no power source wire and plug.

Figure 5:
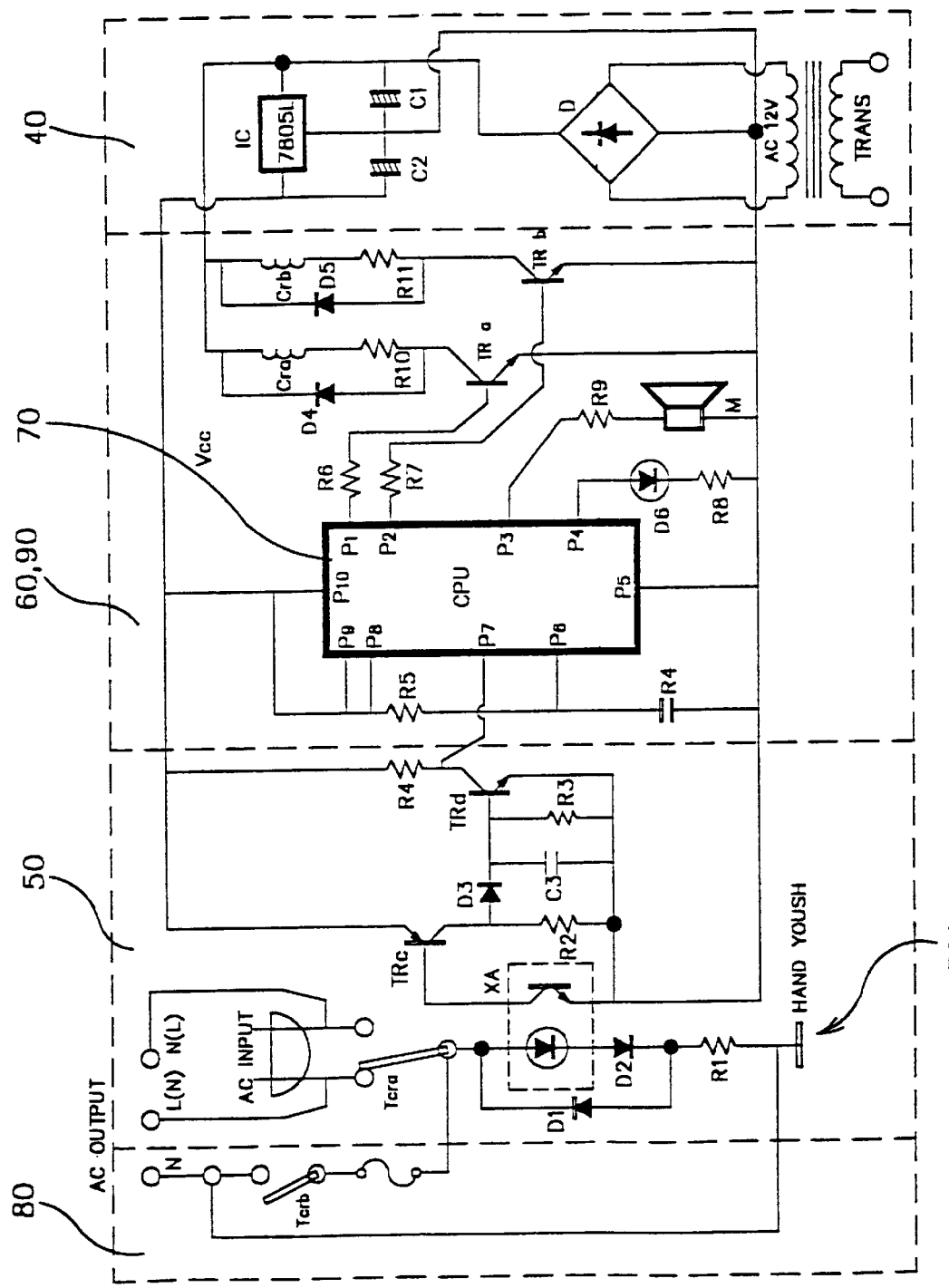
FIG. 5 is a circuit diagram of the present invention.

As show in FIG. 5, the major circuit diagram of the present invention is divided into six parts: a power source system 40, a detecting circuit 50, an actuating circuit 60, a locking circuit 70, a safe circuit 80 and a warning circuit 90, wherein the power source system 40 consisting of a transformer (TRANS), a bridge rectifier (D1), a rectifying capacitor (C1) and a stabilizer IC(7805) is a conventional rectifying stabilizer circuit to convert AC power source into DC power source; the transformer (TRANS.) drops marketable 110V (or 220V) down to 12V AC power source which becomes 16V DC power source through the bridge rectifier (D1), the 16V DC power source is filtered as a smoother and stabilizer DC power source through the rectifying capacitor (C1) and becomes a 5V DC power source through the stabilizer IC (7805) for various small signal circuits. The detecting circuit 50 consisting of a photoelectric converter (XA), an attenuating resistor (R1) and a separate rectifier (D3) is a photoelectric control device as a key part of the present invention to use a central processing unit (CPU) or a conventional control line for detecting the LIFE and NULL of power source respectively in sequence, to wit, to adsorb or release a contact point Tcra through closing or breaking by a transistor Tcra so as to let the contact point Tcra contact the L or N pole of power source respectively. When human body or electronic appliance housing or referable zero potential contacts the touch point 501 and the detecting point contacts the LIFE, if there is a trifling current (about 0.5 to 4 $\mu A$) flowing through the photoelectric converter (XA), separate rectifier (D3), attenuating resistor (R1) and touch point 501 to form a loop, an optical coupler element in the photoelectric converter (XA) will generate a gleam; on the contrary, if the detecting point contacts NULL here is no such gleam. After the optical coupler element of gleam is received by a photoelectric induction element in the photoelectric converter (XA), there is a change of resistance or current, and through the potential change, LIFE or NULL is identified, and such data are transmitted to the central processing unit (CPU) for operation to proceed with the follow-up actuating circuit 60. The photoelectric converter (XA) of the present invention may replaced an optical coupler other photoelectric element. electromagnetic or current sensor or converter.

The actuating circuit 60 is operated by the central processing unit (CPU) and also may be replaced by a conventional line. When a signal from the detecting circuit 50 is collated for two or three times to affirm the LIFE and NULL positions without error, the central processing unit (CPU) issues an order for output to the transist TRa or TRb through an output point so as to actuate a relay Cra or Crb, select the NULL address, drive an electromagnetic contact point Tcra or Tcrb, connect the ground wire to the hole address and enable the ground wire connecting to the ground wire of power source at the output end.

The locking circuit 70 is operated the central processing unit (CPU) and also may be replaced by a conventional line. When the actuating circuit 60 is actuated, the central processing unit (CPU) does not take the detecting signal any more, namely to let the detecting signal disappear, so the circuit has locked the power source NULL until the power source is interrupted or cut off.

The safe circuit 80 is designed to protect the safety of both personnel and computer. When the actuating circuit 60 has an erroneous operation to let the LIFE connect the housing ground point, to wit, the locking circuit 70 beside the LIFE in an unexpected state actuates locking to the ground point, the computer housing has 110V voltage, the output ground end will lead to the housing charge when the computer is turned on, a current larger than 1 ampere will instantaneously passes through the ground point at the output end, and at the same time, the fuse will burn down itself and cut off the locking circuit 70 so as to protect the safety of both computer and personnel. In this circuit 80, the fuse is an overload protective device, and a toggle switch of overload protective device may be also adopted to make its actual use more convenient.

The warning device 90 is also under the control of the central processing unit (CPU) and also may be replaced by a conventional line. When the actuating circuit 60 has not been actuated, the said device 90 buzzes intermittently for warning so as to remind the user to touch the touch point 103 with his hand as shown in FIG. 2 or to await automatic actuating until the actuating circuit 60 is actuated and the locking circuit 70 correctly locks the ground NULL, the warning will stop.

The appearance of examples of the present invention is a box body which can be assembled with the electric appliances in general and contained therein in the design phase thereof so that the function of the present invention can be more widespread to let numerous consumers enjoy convenience and practice, eliminate their worry about suffering the low-frequency radiation and enable them to be safer and live better.

From the foregoing description the design of a power source conversion device capable of eliminating low-frequency radiation according to the present invention is quite out-standing to offer an effective method to eliminate the drawbacks of power source wire and conventional electric appliances in general so as to step up their function which has been left much to be desired.

The examples mentioned above are merely better embodiments of the present invention which cannot be used to limit the scope of putting the present invention into practice, and all the changes and modifications based on the claims of the present invention remain in the scope covered by the claims of the present invention.

What is claimed is:

1. A power source conversion device capable of eliminating low-frequency radiation, comprising:

a power source circuit designed to convert AC power source into DC power source;

a detecting circuit to contact LIFE and NULL ends of power source respectively in sequence through a control circuit for detecting which is LIFE and which is NULL; a touch point is touched through human body or electronic appliance housing or referable zero potential point as a reference potential, if it is LIFE end, there is trifling current flowing through a photoelectric control device to generate a gleam to be received by a photoelectric inductor and resulted in a signal change of resistance or current to be operated by a central processing unit or a conventional line for actuating an actuating circuit; and there is no such phenomenon if it is NULL end;

an actuating circuit to receive signal from the detecting circuit, the central processing unit or conventional line collates LIFE and NULL signals for several times without error and drives circuit operating to let output ground point connect NULL of power source at input end; if the detecting signals disappear during collation, the said circuit will stop operation at once; a locking circuit to lock the actuating circuit to keep it in a actuating state until the power source is cut off;

a safe circuit as an overload protective device can prevent the danger caused by an erroneous circuit operation from happening so as to protect the safety of both personnel and computer;

a warning circuit to warn the user touching a touch point or awaiting automatic actuating to actuate by means of signals before the circuit has not been actuated;

through the foregoing combination, when human body or electronic appliance housing or referable zero potential point contacts the touch point, the circuit communicates with the power source and perform identification, when NULL is detected, NULL is locked onto an output ground point so that the power source in general can automatically finish correct grounding, the electromagnetic screening device in the electric appliance can develop its function to achieve the purpose of eliminating low-frequency radiation and preventing electric leakage from happening.

2. A power source conversion device capable of eliminating low-frequency radiation as claimed in claim 1, wherein the photoelectric control device consists of a photoelectric converter, a separate rectifier and an attenuating resistor.

3. A power source conversion device capable of eliminating low-frequency radiation as claimed in claim 2, wherein the photoelectric converter may be an optical coupler or other photoelectric or element or current sensor or converter.

4. A power source conversion device capable of eliminating low-frequency radiation as claimed in claim 1, wherein the actuating circuit comprises a transistor and a relay as a control circuit, and when LIFE and NULL are firmly identified, the transistor is driven to actuate an electromagnetic contact point of the relay so as to let the ground point connect NULL of power source at input end.

5. A power source conversion device capable of eliminating low-frequency radiation as claimed in claim 1, wherein the referable zero potential point may be a good or poor conductor with a potential equal to the crust such as floor, wall, door and window with aluminum or wooden frame.

\* \* \* \* \*